United States Patent
Fritz et al.

(10) Patent No.: US 6,817,982 B2
(45) Date of Patent: Nov. 16, 2004

(54) METHOD, APPARATUS, AND PRODUCT FOR ACCURATELY DETERMINING THE INTIMA-MEDIA THICKNESS OF A BLOOD VESSEL

(75) Inventors: Helmuth Fritz, Yucaipa, CA (US); Terry Fritz, Boise, ID (US)

(73) Assignee: Sonosite, Inc., Bothell, WA (US)

( * ) Notice: Subject to any disclaimer, the term of this patent is extended or adjusted under 35 U.S.C. 154(b) by 23 days.

(21) Appl. No.: 10/407,682

(22) Filed: Apr. 7, 2003

(65) Prior Publication Data

US 2003/0199762 A1 Oct. 23, 2003

Related U.S. Application Data

(60) Provisional application No. 60/374,223, filed on Apr. 19, 2002.

(51) Int. Cl.[7] .............................. A61B 8/00; G06K 9/00
(52) U.S. Cl. ....................................... 600/443; 382/128
(58) Field of Search .................................. 600/437, 443, 600/447, 463, 466–467; 328/100, 128; 345/215, 419, 660, 664–668

(56) References Cited

U.S. PATENT DOCUMENTS

| | | | |
|---|---|---|---|
| 4,945,478 A | | 7/1990 | Merickel et al. |
| 5,036,463 A | * | 7/1991 | Abela et al. ................. 382/130 |
| 5,203,337 A | | 4/1993 | Feldman |
| 5,345,938 A | | 9/1994 | Nishiki et al. |
| 5,411,028 A | | 5/1995 | Bonnefous |
| 5,462,059 A | | 10/1995 | Ferrara et al. |
| 5,520,185 A | | 5/1996 | Soni et al. |
| 5,533,510 A | | 7/1996 | Koch, III et al. |
| 5,544,656 A | | 8/1996 | Pitsillides et al. |
| 5,569,853 A | | 10/1996 | Mignot |
| 5,669,382 A | | 9/1997 | Curwen et al. |
| 5,687,737 A | | 11/1997 | Branham et al. |
| 5,712,966 A | | 1/1998 | Nadachi |
| 5,724,973 A | | 3/1998 | Spratt |
| 5,800,356 A | | 9/1998 | Criton et al. |
| 5,952,577 A | | 9/1999 | Passi |
| 6,048,313 A | | 4/2000 | Stonger |
| 6,048,314 A | | 4/2000 | Nikom |
| 6,120,445 A | * | 9/2000 | Grunwald ................... 600/437 |
| 6,132,373 A | | 10/2000 | Ito et al. |
| 6,165,128 A | * | 12/2000 | Cespedes et al. ........... 600/463 |
| 6,200,268 B1 | * | 3/2001 | Vince et al. ................ 600/443 |
| 6,264,609 B1 | | 7/2001 | Herington et al. |
| 6,287,259 B1 | * | 9/2001 | Grunwald ................... 600/437 |
| 6,301,498 B1 | | 10/2001 | Greenberg et al. |
| 6,346,124 B1 | | 2/2002 | Geiser et al. |
| 6,354,999 B1 | | 3/2002 | Dgany et al. |
| 6,381,350 B1 | | 4/2002 | Klingensmith et al. |
| 6,405,071 B1 | * | 6/2002 | Analoui ...................... 600/425 |
| 6,443,894 B1 | | 9/2002 | Sumanaweera et al. |
| 6,450,964 B1 | | 9/2002 | Webler |
| 6,459,805 B1 | * | 10/2002 | Reynolds et al. ........... 382/128 |
| 6,512,841 B2 | * | 1/2003 | Yamada et al. ............. 382/128 |
| 6,514,202 B2 | * | 2/2003 | Grunwald ................... 600/437 |
| 6,730,035 B2 | * | 5/2004 | Stein .......................... 600/449 |
| 2001/0009977 A1 | | 7/2001 | Sato et al. |
| 2002/0086347 A1 | | 7/2002 | Johnson et al. |
| 2002/0115931 A1 | | 8/2002 | Strauss et al. |
| 2002/0180764 A1 | * | 12/2002 | Gilbert et al. .............. 345/660 |
| 2004/0116813 A1 | * | 6/2004 | Selzer et al. ................ 600/467 |
| 2004/0122326 A1 | * | 6/2004 | Nair et al. .................. 600/467 |

* cited by examiner

*Primary Examiner*—Francis J. Jaworski
(74) *Attorney, Agent, or Firm*—Fulbright & Jaworski L.L.P.

(57) ABSTRACT

An apparatus, automated method technique and product for accurately determining the intima-media thickness of a blood vessel.

29 Claims, 2 Drawing Sheets

METHOD, APPARATUS, AND PRODUCT FOR ACCURATELY DETERMINING THE INTIMA-MEDIA THICKNESS OF A BLOOD VESSEL

RELATED APPLICATIONS

This application is a continuation-in-part of the provisional patent application entitled "Method and Apparatus for Accurately Determining the Intima-Media Thickness of a Blood Vessel" filed Apr. 19, 2002, Ser. No. 60/374,223.

BACKGROUND OF THE INVENTION

1. Field

This invention pertains to methods and apparatuses related to measuring the intima-media thickness of carotid arteries to diagnose arterial sclerosis using digitally captured images from an ultrasound device inputted into and analyzed by a computer algorithm. In particular it pertains to a computer device digitally analyzing the inputted digital ultrasound image via various pixel algorithms.

2. State of the Art

A number of manual and automated measuring methods of intima-media thickness of carotid arteries to diagnose arterial sclerosis systems are known. These devices employ an ultrasound device for generating digital and/or analog images of the carotid arteries, which are then manually measured or automatically analyzed. The manual measurements are time consuming and require a trained analyst to perform the analysis. Hence, the need for a device to automatically measure and analyze the digital ultrasound images.

Masao et al., U.S. Pat. No. 6,132,373 discloses an automated intima-media thickness computer measuring apparatus and arterial sclerosis diagnosing system of the digital pixel data of ultrasound images of the carotid artery. Masao et al has the following shortcomings, which are overcome by the present invention, as described below:

- Ultrasound machine requires a digital capture card that interfaces with a corresponding PCI adapter card on the PC to transmit digital images. The present invention does not require a digital capture card. It only requires some mechanism to capture images from an ultrasound machine. These mechanisms could include recording to video tape, sending the video out to a analog capture device, or sending data directly to a computer via a serial cable, USB cable, a 1394 cable, a wired or wireless network, or any other standardized communications medium.
- Searching for adventitia starts from a user-specified position and only searches a pre-determined number of pixels. The thickness of the adventitia can be quite large. Searching only a predetermined number of pixels could stop short of the actual adventitia for a thick intima-media layer. The present invention starts by searching for the adventitia first by looking for the brightest portion of the image. Its search region is not limited to a predetermined number of pixels.
- The Masao et al algorithm has no mention of a calibration process. This implies that the algorithm Masao et al use can only be used at a single resolution and only on the machine that the algorithm is written for. The present invention requires the user to calibrate the pixel size to ensure that any image from any ultrasound machine can be used to accurately measure IMT. Additionally, the present invention can automatically calibrate the pixel size if the image comes from a recognized ultrasound device. This is accomplished by looking at precise known locations for calibration markers that exist on images output from certain ultrasound devices. If these exact patterns are found, the calibration process is automatic, precise and error free.
- The Masao et al algorithm locates the intima using a second maximum. The second highest maximal peak of image values from the lumen to the adventitia does not work if the intensity values do not have local maximum points at all, but rather gradually slope upward from the lumen to the adventitia. Applicants have seen many instances where this is the case. The present invention's algorithm solves this by looking for the largest local gradient to determine the lumen/intima boundary.
- The Masao et al algorithm is very sensitive to where the user specifies the vertical location of the base position. If the user specifies a too high base position, the predetermined search distance will not search down far enough to find the adventitia. If the user specifies too low of a base position, the lumen/intima boundary may not be found correctly. The present invention solves this issue by looking first for the brightest spot in the image in a relatively large region about the user specified location. This significantly reduces the criticality of the user specified vertical location.
- If the second maximal intensity peak (the peak corresponding to the intima location) is not found for a given column, the corresponding column of pixels is ignored under the Masao et al algorithm. By doing this, their algorithm could ignore a crucial location of the media/adventitia boundary, and information is lost. By throwing away information, one reduces the degree of accuracy of the measured IMT. The present invention essentially fills in these gaps at the lumen/intima boundary using neighboring column information for poor contrast regions to allow a column of data to not be ignored. This allows the media/adventitia boundary information to still be used if its data is of good quality.
- Masao et al's regression curve fit algorithm uses a cubic polynomial curve fit across the entire measurement range of data. If the measurement range is small, this is fine. But if the measurement range spans multiple millimeters, this curve fit falsely restricts the shape of the intima-media layer. The present invention uses a piecewise curve-fit interpolation to allow an unbounded measurement range while still smoothing the interface boundaries and not artificially limiting the potentially tortuous nature of the intima-media layer.
- Masao et al allows no user intervention for poor quality images. The present invention allows the user to intercede in the computer's behalf for poor quality images to allow accurate measurements to still take place by using the advantage of the human's visual pattern matching abilities to limit where lumen/intima and media/adventitia boundaries can lie.
- Masao et al uses a single column of pixels independently to determine the location of the intima, adventitia, media/adventitia boundary and the lumen/intima boundary locations are. The present invention's algorithm finds the location of the adventitia by using adjacent column's pixel intensity information. This significantly reduces false adventitia location errors due to noise and/or poor contrast in the digital image. It also tracks the bottom of the media layer using neighboring pixel information to assist in segmenting the search region for the lumen/adventitia boundary from the media/adventitia boundary.

Masao et al determines the IMT by averaging only three values: the maximum IMT value, and two other non-maximal IMT values. The present invention uses the distance from the lumen/intima boundary to the media/adventitia boundary for every column in the measurement region to more accurately determine the true value of the IMT. This approach takes into account all portions of the tortuous shape of the intima-media along the entire measurement range, which directly improves the measurement accuracy.

Masao et al addresses none of the 8 operator associated factors. Without compensating for these factors, the ultimate accuracy of IMT measurements is significantly reduced. The present invention discusses these factors and describes how to minimize the effects.

Pitsillides et al., U.S. Pat. No. 5,544,656 discloses a closed-loop single-crystal ultrasonic sonomicrometer capable of identifying the myocardial muscle/blood interface and continuously tracking this interface through the cardiac cycle using a unique piezoelectric transducer. The echoes from the transducer are amplified and amplified and applied to a Doppler decoder, which analyzes the signals to determine myocardial wall thickness throughout the cardiac cycle. Criton et al., U.S. Pat. No. 5,800,356 discloses an ultrasonic diagnostic imaging system with Doppler assisted tracking of tissue motion providing a method for tracing the border of tissue through temporarily acquired scan lines comprising the steps of reducing noise in the scan lines, producing a map of tissue edges from the scan lines, denoting a tissue border to be traced, and using velocity information corresponding to tissue edges to trace the denoted border. Sumanaweera et al., U.S. Pat. No. 6,443,894B1 discloses a medical diagnostic ultrasound system and method for mapping surface date for three dimensional imaging by boundary structure determined from one type of energy such as Doppler energy data. Another type of data representing the boundary or an area adjacent the boundary is then extracted or identified to provide texture mapping onto or adjacent the boundary.

Nadachi, U.S. Pat. No. 5,712,966 discloses a Medical Image Processing Apparatus, which includes a color video monitor to display color densities of blood vessels. Koch, III et al, U.S. Pat. No. 5,533,510 discloses an ultrasound display apparatus providing a two-dimension display of a fluid filled cavity and surrounding wall tissue in the form of a sequence of pixel image frames that are shown on a display screen. Different color values are then used from frame to frame on both ventricular expansion and contraction cycles. Herrington et al., U.S. Pat. No. 6,264,609B1 discloses an ultrasound apparatus and method for tissue characterization of tissues, tissue transitions and tissue constituent structures employing Fourier frequency bands of the power spectrum of digitized pulses of returned energy.

Soni et al., U.S. Pat. No. 5,520,185 discloses a method for enhancing an intravascular ultrasound blood vessel image system where ultrasound echoes representing vessel walls are distinguished from ultrasound echoes from blood by using a classifier which employs the mean and variance of the raw data of gray intensities as acquired directly from an ultrasound scanner detector. Stonger, U.S. Pat. No. 6,048,313 discloses a method and an apparatus for increasing the contrast resolution of computer-generated images using fractal enhancement techniques. Each image frame is divided into blocks of pixels which are sorted into source and destination lists based on their distance from the transmit focal zone.

Nikom, U.S. Pat. No. 6,048,315 discloses an automated measurement and analysis of patient anatomy based on image recognition by generating an ultrasound image of a region of a patient and provides coordinates of walls of vessels in the image. In response to placement of a cursor within the vessel in the ultrasound image, one or more parameters of the vessel in the vicinity of the cursor are determined automatically from the wall coordinates. The determined parameter values are then recorded such as vessel diameter, vessel center coordinates, and/or vessel wall directions. The vessel may be automatically mapped by moving the cursor to multiple positions along the vessel and determining the parameters of interest at each cursor position. The smallest vessel diameter may be determined and highlighted in the ultrasound image. Curwen et al, U.S. Pat. No. 5,669,382 discloses a system for measuring myocardium in cardiac images by employing a "goodness function" analysis of the pixels imaging via calculations of the second derivative and fourth derivatives of radial change due to a change in angle. Spratt, U.S. Pat. No. 5,724,973 discloses a method and apparatus for ultrasonic measurement of vascular diameters generating a plurality of trial diameters, which are then correlated to the inner and outer regions of each trial diameter.

Klingensmith et al, U.S. Pat. No. 6,381,350 B1 discloses an intravascular ultrasonic analysis using active contour method and system wherein the user selects boundary points on the image believed to be locations of the luminal bound, and a boundary contour is generated based on boundary points, which is then optimized by adjusting the boundary points based on a radially determined edge of the luminal boundary performed on the image in polar format. Once the final luminal boundary contour is generated the process is repeated to determine the medial-adventitial boundary contour. With is contour data, the percent of occlusion caused by plaque is determined. The objectives of this patent are similar, but the measurement methodology differs.

Mignot, U.S. Pat. No. 5,569,853 discloses an ultrasonic measuring apparatus that includes an ultrasonic transducer for emitting ultrasonic pulses at a predetermined repetition frequency towards an object have a plurality of walls such as a blood vessel, receiving echoes reflected from such walls, and producing an echo signal having a plurality of elementary echo components, which a digitizer digitizes the echo signal into a series of digital values that are stored in a buffer memory under a control circuit. A computer transfers the series of digital values into a memory for subsequent computer processing to remove a group of digital values digitized between consecutive elementary components from those digital values to be treated between consecutive pulses.

Cited for general interest is Dgany et al., U.S. Pat. No. 6,354,999B1, which discloses a System and Method for Detecting Localizing, and Characterizing Occlusions and Aneurisms in a Vessel via introducing an artificial pressure or flow excitation signal into the blood vessel and measurement and analysis of the pressure and or flow. Greenberg et al., U.S. Pat. No. 6,301,498B1 discloses a method and apparatus for generating a three-dimensional shape of an artery comprising the step of obtaining at least one angiographic X-ray image of an artery cross section, so that there are lines that define the walls of the artery which have data representing X-ray intensity that can be used to determine artery thickness; gathering the data and inputting that date into a computer; using the data to create a three-dimensional image of the artery. Nishiki et al., U.S. Pat. No. 5,345,938 discloses another diagnostic apparatus for circulatory systems employing both an X-ray diagnostic system and an ultrasonic diagnostic system.

Passi, U.S. Pat. No. 5,952,577 discloses an ultrasonic imaging system for imaging an object via an ultrasonic swiveling probe. Sato et al, U.S. Publication No. 2001/0009977A1 discloses an ultrasound diagnosis apparatus including an ultrasound probe and a beam-former configured to scan an object to be examined with ultrasound waves through the ultrasound probe.

Bonnefous, U.S. Pat. No. 5,411,028 discloses an ultrasonic echograph used as a profilometer for the measurement of the instantaneous blood flow rate and the instantaneous radius variation and mean radios of the artery.

Granham et al, U.S. Pat. No. 5,687,737 discloses a computerized three-dimensional cardiac mapping with interactive visual displays. Feldman, U.S. Pat. No. 5,203,337 discloses a coronary artery imaging system in which a catheter is provided with a forward looking sonic transducer for measuring fluid flow in arteries without disturbing the flow and a side looking sonic transducer for imaging the arterial walls.

Merickel et al, U.S. Pat. No. 4,945,478 discloses a non-invasive medical imaging system and method for the identification and 3-D display of Artherosclerosis and the like employing an image processing, pattern recognition and computer graphics system and method using multi-dimensional Magnetic Resonance Imaging (MRI).

Geiser et al, U.S. Pat. No. 6,346,124B1 discloses a method for generating a synthesis echocardiographic image comprising first obtaining, for a plurality of pathologically similar reference hearts, a reference echocardiographic image of each reference heat at end-systole and end-distal. The coupled epicardial and endocardial borders are then identified in each echocardigraphic image An epicardial/endocardial border pair is then modeled and mapped.

Johnson et al, U.S. Publication No. 2002/0086347A1 discloses a method for quantitative analysis of blood vessel structure via geometrical measurement of blood vessel images. Strauss et al, U.S. Publication No. 2002/0115931A1 discloses a method of localizing a lesion in a body lumen comprising proving an image of the body lumen, acquiring information about the lesion with a detection device, and displaying the information in a spatially correct distribution relative to the image of the body lumen.

Webler, U.S. Pat. No. 6,450,964B1 discloses an apparatus and method for determining the angular position of a sensor within a catheter.

The invention described below outlines how the device and automated method achieve the above objectives to avoid the need for time consuming manual measurements, which require a trained analyst.

Definitions

As used herein, the following terms have the defined meanings:

IMT: Intima-media thickness

Digital image: A plurality of values that represent a series of rows and columns that when displayed represent an actual image. Each value is typically a single number, a triplet, or a quadruplet of numbers that represents the gray-scale intensity or color of the image at the corresponding location. These numbers typically range from 0 to 255. They can also range from 0 to 1, 0 to 16, 0 to 65535, or many other ranges.

Pixel: A single value or set of values that are inherently coupled to represent a single intensity, color and/or gradation in a Digital Image. The "values" described in the definition of "Digital Image" above are referred herein as pixels.

Software: The computer program that takes digital images as input and computes the IMT.

User/Operator: The person operating the software by viewing the computer screen and specifying commands via the input devices, which can include a keyboard and/or a mouse.

SUMMARY OF THE INVENTION

The invention comprises an ultrasound device for outputting digital image data representing an image of the blood vessel produced by scanning the blood vessel with an ultrasound device, and a computer analyzing device for receiving the output digital image data and calculating the intima-media thickness of the blood vessel according to an algorithmic analysis of the received digital image data. It employs a blood vessel measurement system, typically including:

1) Ultrasound machine for capturing digital images of blood vessels, typically the carotid artery. A digital image of a longitudinal view of a blood vessel contains dark and light regions in the image, which represent differing densities of tissue. The brightest portion of the ultrasound image typically corresponds to the densest part of the tissue that is being measured. When capturing a digital image of a blood vessel using an ultrasound technology, the brightest portion of the images typically corresponds to the walls of the blood vessel itself. The wall of the blood vessel itself has three different regions. The portion of the wall of the artery that is adjacent to the blood flow is the intima. The next layer after the intima is the media. Finally, after the media is the adventitia. When viewing an ultrasound image of a blood vessel, the adventitia typically shows up as the brightest portion of the image. Usually the far wall of the blood vessel (the wall furthest from the skin, and hence the ultrasound probe) is the clearest, and hence is typically where the measuring of the IMT is accomplished.

2) Means for transferring image data from ultrasound machine to computer.

3) Computer running software application that contains a sophisticated algorithmic based measurement apparatus to measure the intima-media thickness (IMT) of a blood vessel wall using the digital images originating from ultrasound machine.

4) A report generating apparatus to allow a patient to quickly receive a report stratifying the patient's generalized vascular atherosclerotic burden and comparing the patient's IMT value with the general population.

5) A database apparatus that standardizes the general population data pool as well as the patient follow up on how a person's IMT varies over time.

The preferred Algorithm employed is as follows:

Pre-Work

Step 1: Calibrate the software application by specifying two pixels in the digital image and also specifying what the corresponding physical distance is between these two pixels. This calibration process allows any image to be used by the software application as long as two calibration points can be placed on the digital image from the ultrasound machine at a known distance from each other (this is usually a standard feature of ultrasound devices). Once the calibration procedure is completed, each pixel has an associated dimension in width and height (we assume the pixels are square from the ultrasound machine). A variation would be to have both a vertically and horizontally calibration process to handle non-square ultrasound pixels. If multiple digital images are being processed from the same ultrasound machine using the same capture resolution, the calibration process needs to be completed only once per series of such common images. Another variation is to have the software application automatically calibrate the pixel size of each analyzed image based on known landmarks contained in the image. This is most useful when the software application is known to be used with a given ultrasound device that has characteristic landmarks or calibration anchor points. If each of the ultrasound scale modes or zoom modes has unique markers on the image, the software can determine which of the scale modes the image was captured from, and therefore can know implicitly the calibration distance between these two points. Then, the software application can "count" the number of pixels between these landmarks and determine the calibrated image pixel size.

Step 2: Have the user specify the center of the measurement region by clicking the mouse in an area near the blood vessel wall. The vertical location of this pixel click is not too important since it is used to determine which blood vessel wall will be measured (the blood vessel wall nearest in vertical location in the digital image to the user's click is the wall to be measured). The horizontal location of the user's click is what is used as the center of the measurement region where the IMT will be computed. A variation on this step would be to automate where the measurement is to be taken. One approach would be to center the measurement region horizontally in the digital image. This would determine the horizontal position. The vertical position could be located several different ways. One way would be to find the brightest pixels in the column of pixels at the horizontally specified location where the center of the measurement region starts. This would likely be the blood vessel wall with the highest degree of contrast and hence the wall with the best characteristics for automatically measuring IMT. It is preferable to specify where the measurement region will be centered as apposed to automatically determining this location.

Step 3: Compute an image intensity histogram in the region about the user's mouse click (or automated starting position). This search region should be tall enough to guarantee that the lumen intensities are used as well as large enough to ensure that adventitia intensities are used. It should also be wide enough to ensure a good sampling of pixels intensities. A good width we found was the measurement region. A good height was ½ to ¼ of the measurement width. We then compute the minimum and maximum intensity seen in this region about the users click. We will use these intensities in the following algorithm's steps.

Step 4: Have the user specify a measurement width. This can be automatically setup to be a given width and is overridable to allow the operator to adjust the measurement width depending on image quality. A good measurement width default is 5 mm, although this default is modifiable by the operator. This is approximately the diameter of most people's carotid artery.

Algorithm Sequence

First step: Automatically locate the adventitia along a horizontal area where the measurement of the IMT will take place. This is accomplished by starting from a horizontal position that the user of the software indicates by clicking the mouse in the image area at the center of the measurement region. Follow the maximum intensity region, which represents the area inside the adventitia. This following algorithm starts from a horizontal position specified by the user (horizontal will be used to specify a direction along the length of the artery). The adventitia location algorithm creates a connected set of pixels extending both to the left and to the right of the horizontal location specified by the user. The algorithm allows the pixels to wander up and down from adjacent pixels by no more than a predetermined amount to avoid jumping to a neighboring bright area. This algorithm is similar to following a path of bread crumbs and not allowing following any bread crumbs that are too far off from the current direction you are traveling. This allows for turns and twists without creating disjoint breaks in the pixel path. The searching is accomplished by finding the brightest pixel in the column of pixels where the user specified where the center of the measurement region is to begin. Then, from this brightest pixel, a path is started to the right and continues a distance that is one half of a user specified measurement width. The path also extends to the left from the user specified center of the measurement region and continues a distance that is one half of a user specified measurement width. When both the left and the right path are traced out, the entire path that specifies the center of the adventitia has been created that is a width equal to the user specified measurement width. In tracing the path, the tracing algorithm proceeds a single pixel at a time. To find the next pixel in the path, the algorithm looks in the adjacent column of pixels for the brightest pixel within a bounded range above and below the current brightest pixels vertical location. This constrains the next pixel from jumping to an adjacent bright spot that may be a single island of bright pixels. The adventitia pixel path contains only one pixel per column, and also has one pixel in every column that is within the horizontal range of pixel columns that constitute the measurement region. Since the blood vessel in the captured images is typically near horizontal, this is a reasonable approach.

First step variation 1: If the tendency of the path of pixels demarking the adventitia is following a sloped up or down path, allow the search for the next adjacent pixel to be skewed in the direction that the path is following i.e. if the path is heading down to the right, allow the vertical search region for the next column's bright pixel to be skewed in the downward direction. This prevents false sharp changes in direction in the adventitia.

First step variation 2: When searching for the next pixel composing the adventitia pixel path, it can be useful to search more than a single pixel ahead to help reduce the possibility of getting lost in less bright regions. This can also help in bridging adventitial gaps due to image noise.

First step variation 3: For images that tend to be noisy, the operator can specify a slope as well as a first pixel starting position to help assist in the adventitia tracking algorithm to not veer off course from the actual adventitia pixel path.

Second step: Curve fit adventitia pixel path. Since the adventitia can be non-linear in shape, we want to allow a varying path of pixels while at the same time reducing the noisy variations in image brightness that might not truly represent the adventitia. To solve this problem, we apply a curve fitting algorithm to smooth the adventitia pixel path. The curve fit algorithm we use is an overlapped, piecewise $2^{nd}$ order polynomial curve fit. Since the measurement width is typically many pixels in width, we don't want to constrain the entire width to a $2^{nd}$ order polynomial curve fit since that would artificially smooth out bumps and valleys that exist in the adventitia. We also don't want to use a higher order polynomial since that would add computational complexity that we feel is not needed.

Third step: Locate lumen. Once the pixel path of the adventitia is found and smoothed using curve fitting, we take each column of pixels independently within the measurement range starting from the pixel in the column that is part of the adventitia pixel path. Then, we search toward the center of the blood vessel (the user is required to click on the inside of the blood vessel near the wall of the blood vessel, which is what gives us the direction to search looking for at least 4 pixels that are darker than a minimum threshold value indicating the presence of lumen. The minimum threshold value is a value that is computed as follows: minimum threshold= minimum intensity+0.2*(maximum intensity− minimum intensity). Once we find 4 pixels that are less than the minimum threshold value, we mark the first one we found as the position of the lumen in the current column of pixels. When this is completed, we have a series of pixel locations across the measurement region that specifies the location of the lumen. There is exactly one and only one pixel in each column in the measurement region that specifies the location of the lumen. We will call this series of pixels the lumen pixel path. An alternative would be to have the minimum threshold be user configurable using either a scroll bar that chooses a value between a minimum and maximum value or by explicitly setting a value through a user interface input mechanism i.e. an edit box.

Third step alternative 1: Combine an additional requirement that the lumen/intima boundary must be adjacent to a significant intensity gradient representing the abrupt boundary of the intima to lumen transition. This is a useful technique when the lumen contains large amounts of noise.

Third step alternative 2: Add the ability to sense regions in the intima/lumen boundary where a large contrast is not visible. Let's call this region of poor contrast a gap. If the gap is small enough, the algorithm is allowed to search beyond the gap along the same slope that this intima/lumen boundary was heading to try and pick up the next high contrast region between the intima and lumen. A gap must not have an adjacent region of a bright pixels in the lumen, since the gap would really be a pocket in the intima/media region.

Third step alternative 3: Add the ability to simultaneously sense "large contrast" horizontal regions that are at least 3 pixels wide and vertically deviating not more than 3–5 pixels between adjacent regions of the intima/lumen boundary along the entire length of the specified measured segment even though these segments may exist in a patchy distribution along the entire length of the specified measured segment. The aggregate total length of the "large contrast" regions must be greater than "less contrast" regions. Then a specified limiting algorithm "fills in" the "less contrast" regions by applying a narrow range of possible vertical deviation based on usual maximal contrast change within those "less contrast" segments. If there is no significant graded contrast within any "less contrast" regions then the "gap" regions are simply bridged" between adjacent "large contrast" regions. The lateral limits of the measured segments must always include "large contrast" regions.

Fourth step: Curve fit lumen pixel path. We curve fit the lumen pixel path just like step two above to reduce any noise due to dark regions in the intima or media that were marked as lumen pixels. Curve fitting the lumen pixel path using an overlapped, piecewise $2^{nd}$ order polynomial curve fit gives a nice boundary of where the edge of the lumen is that backs up right against the intima.

Fifth step: Locate dark region at the bottom portion of the media layer. This operates on each column of pixels in the measurement region. For each of these columns, this step starts from adventitia pixel and searches about ⅔ of the way to the lumen pixel. Since the adventitia pixel is by definition one of the brightest pixels in the column of data, each pixel moving away from the adventitia pixel will tend to get darker There will be a pixel in the column of pixels that will be a first minimum in intensity when searching in this manner. If this first minimum is at least as dark as the media dark threshold value, this is the location of the media dark region. The media dark threshold is defined as: media dark threshold=minimum intensity+0.4*(minimum intensity+maximum intensity). If the first minimum in intensity is not as dark as the media dark threshold, the next minimum intensity point is searched for. This continues until a minimum intensity pixel is found that is darker than the media dark threshold or until the pixel that is ⅔ of the way to the lumen pixel is reached. If we have not found media dark region pixel by the ⅔ point, the ⅔ point is defined as the media dark region. Call this set of media dark region pixels the media dark pixel path. An alternative to this step would be to have a user adjustable configuration for the dark threshold. This may be in the form of a scroll bar that moves from a minimum value to a maximum value. The user may also specify the dark threshold by entering a number into an edit box or other user interface input mechanism.

Sixth step: Curve fit the media dark pixel path. This is accomplished using the same curve fit strategy as in step two and step four.

Seventh step: Locate lumen/intima boundary. This is done on each column of pixels in the measurement region. To locate the first pixel that is part of the intima coming from the lumen pixel, search from the lumen pixel toward the dark pixel in the corresponding column of pixels. When the largest positive change in pixel intensity is found before a local maximum in the pixel intensities is found, this is considered the first pixel in the intima layer (the pixel at the lumen/intima boundary). We only search up to the first local maximum in intensity values since there can be many local minimum and maximum points between the lumen/intima boundary and the media/adventitia boundary. Once the first pixel in the intima is found in this manner for every column of pixels in the measurement region, these set of pixels are called the intima pixel path.

Seventh step alternative 1: A reference lumen boundary point is determined by the operator by clicking on a point in the lumen just beyond the visible intima/lumen border. Now along the entire length of the measured segment, one applies the "third step alternate 3" process as described above.

Eighth step: Locate the media/adventitia boundary. This is done on each column of pixels in the measurement region. To locate the media/adventitia boundary, search for the largest positive change in pixel intensity up until a local maximum in the pixel intensities is found. This maximum intensity change is considered the pixel closest to the media/adventita boundary. Once this maximum intensity change is found in this manner for every column of pixels in the measurement region, these set of pixels are called the media/adventitia boundary.

Ninth step: Determine the distance between the lumen/intima boundary and the media/adventitia boundary for each column in the measurement region. Then, average all of these distances across the measurement region to determine the overall IMT for the measurement region.

Tenth step: If a slope was specified, modify the resulting IMT by multiplying by the sine of the slope angle, where 0 degrees is a slope parallel to the horizontal axis.

The following other Additions/Alternatives to Algorithm may be employed:

For images with poor contrast or signal-to-noise ratio, it can be very difficult to measure the IMT in a completely automated fashion. Therefore, an alternative is to manually assist the automated algorithm in varying steps. This manual assist mechanism is only used when the operator determines that the automated IMT calculation is obviously wrong. The varying manual steps could include assisting in: 1) locating the adventitia, 2) locating the lumen, 3) determining the curvature/slope of the intima/media layer, 4) constraining the search region for the lumen/intima boundary, 5) constraining the search region for the media/adventitia boundary, 6) increasing, decreasing or laterally moving the region of measurement to find a less noisy region of the intima/media layer. 7) strengthening the aggressiveness (more boldness) with which the various "horizontal" pathways parallel to vessel wall can continue through even lower contrast regions.

Add the ability to determine if an image is too "noisy". The noisiness of the image can be computed and displayed to the operator as an indication of the confidence in the automated algorithm. If the confidence is too low, the operator is advised to either assist the algorithm in a manual fashion or to ignore this image altogether. Several methods for displaying the confidence are: 1) A color coded indicator that varies in colors from a low confidence color like red, to a high confidence color like green, 2) A numerical display of confidence as a percentage, where a low percentage would indicate a poor confidence and a high percentage would indicate a high confidence, 3) A status indicator in the form of a "gas gauge" that displays the confidence on a range from poor to excellent.

One mechanism for determining the "noisiness" of an image (which is used in the previous item) is to automatically or manually locate the lumen, find its boundaries, and perform a histogram of the color values contained in the lumen. If the standard deviation (or variance) would then give a direct indication of noisiness. Since the lumen tends to be a consistent density (blood density is relatively constant), the wider the range of intensity values which directly correlates with the standard deviation of the lumen values, the noisier the image is. Noise can come from a variety of sources including: 1) A large gain setting on the ultrasound machine, 2) Poor data transfer from the ultrasound machine to the digital image, 3) poor quality crispness of borders caused by rapid motion artifact during image acquisition.

Constrain the search region to the portion of the image that only contains the imaged tissue. Typically, an image that originates from an ultrasound machine contains descriptive text, graphs of intensity values, tick marks and other pixilated data that does not constitute the raw measurement data of the tissue. By determining the boundaries of the measured tissue intensities within the entire image, this helps to constrain the automated algorithm from incorrectly searching data that is not part of the blood vessel tissue.

Filter the image before processing for a number of reasons. These include: 1) Low pass filter to reduce overall noise of the image, 2) median filter to reduce isolated noise spikes in the image, 3) an edge detection/embossing filter which highlights edges and can assist in locating boundaries between the lumen/intima/media/adventitia, 4) lateral filter applied in a direction tangent to the blood vessel to reduce noise in a biased direction to prevent loss of edge data perpendicular to the blood vessel direction.

Smooth the resulting boundary lines with a variety of mechanisms. These might include: 1) Simple low pass filter to reduce harsh look of boundaries, 2) median filter to remove single spikes from boundary lines, 3) anomaly filter to remove deviations in the boundaries that are significantly taller than they are wide.

For very noisy images, the addition of a trace mode in which the user traces what he/she perceives the IMT borders to be. Then, the software application takes these input first guess boundaries and tries to find the best set of edges within some constrained distance from the user selected boundaries. The user can adjust how close the computed edges must stay to the user specified boundaries.

Another feature that can be employed to determine the quality of the automated measurement is the nature of the pixel intensities in and around the neighborhood of the measured intima-media layer. By computing a histogram completely encompassing the measurement region as well as including a margin of pixels around the measurement region, a quality factor can be determined. This could communicated to the user by just displaying this histogram and training the operators what "good" IMT histograms look like. This could also take the form of a database of "high quality", "medium quality" and "poor quality" histogram shapes and apply a correlation operation on the measured histogram against the patterns of known histograms. The degree to which the measured histogram matches the good, medium or high quality "standardized" IMT histogram shapes would directly result in a confidence rating that could be communicated to the operator. This would be useful to ensure the operator takes a second careful look at images that the software application thinks is a low or even a medium quality set of intima-media boundaries.

Operator Dependent Factors

The method and apparatus may employ the following to addressing operator dependent Factors that reduce accuracy:

Ultrasound instrument TGC and overall power gain settings: During image acquisition it is important to minimize the gain between extremes of high or low. Gain appears to be able to affect the reported IMT value by up to 10% if not recognized and corrected.

Length of measured IMT segment. Length of measured segment cannot always be the ideal 10 mm so when it is less than 10 mm, the true IMT value changes in a direct but non-linear relationship to the IMT thickness and the distance proximal to the CCA dilation landmark position. This factor can account for as much as 15% variability in reported IMT if not recognized and corrected.

Distance from CCA dilation landmark position to the measured IMT segment. Anatomically the IMT varies in a non-parallel, non-linear fashion along it's final approximate 20 mm proximal to the CCA dilation position. This factor can account for as much as 40% variability in reported IMT if not recognized and corrected (see "IMT compensation as a function of distance from dilation" below for a detailed description on how to compensate for this potential variability factor).

Probe angle positions in relation to the neck surface during image acquisition. Because of the anatomically eccentric variation in IMT thickening, this factor can account for as much as 50% variability in reported IMT if not recognized and corrected.

Head position during image acquisition. This factor can affect the reproducibility on dual run exams by as much as 20% if not recognized and corrected.

Including Near wall measurements. Though technically more challenging and not as clearly defined in most cases, including the near wall measurement for true atherosclerotic burden stratification can affect the reported IMT by as much as 40% if not recognized and corrected.

ECG synchrony. The IMT varies within each cardiac cycle by about 10%. This factor can affect the reported IMT by as much as 10% if not recognized and corrected.

Cross-sectioning the maximal CCA diameter. Unless one is measuring the IMT at it's true point corresponding to the maximal diameter of the vessel, the reported IMT can vary by as much as 15% unless recognized and corrected.

Hence, one could report IMT values obtained without compensating for these factors that were significantly different between measurements on the same person between dual runs if the above 8 factors were overlooked. For example, the difference between reporting an IMT value of 0.7 versus a 0.8 is 13.3%.

Mechanisms for Transferring Ultrasound Image Data to Computer Employing Automated Algorithm The invention may employ a conventional global communication network to transmit off-site measurements to a remote location for digital analysis via a modem, network card, blue tooth interface or any other interface hook-ups to any known data transmission networks such as terrestrial and wireless phone networks, optical data transmission networks, local area networks (LAN), wide area networks (WAN) and all other known and unknown transmission networks and mediums to access a central computer. This allows flexibility in staffing and optimisation of equipment usage. The images may also be transferred via mobile and/or portable media. This would include CD-R's, portable hard drives, flash memory devices (compact flash, smart media, memory stick, etc.), floppy disk, Iomega disk, etc.

DESCRIPTION OF THE ILLUSTRATED EMBODIMENTS

Figure 1:
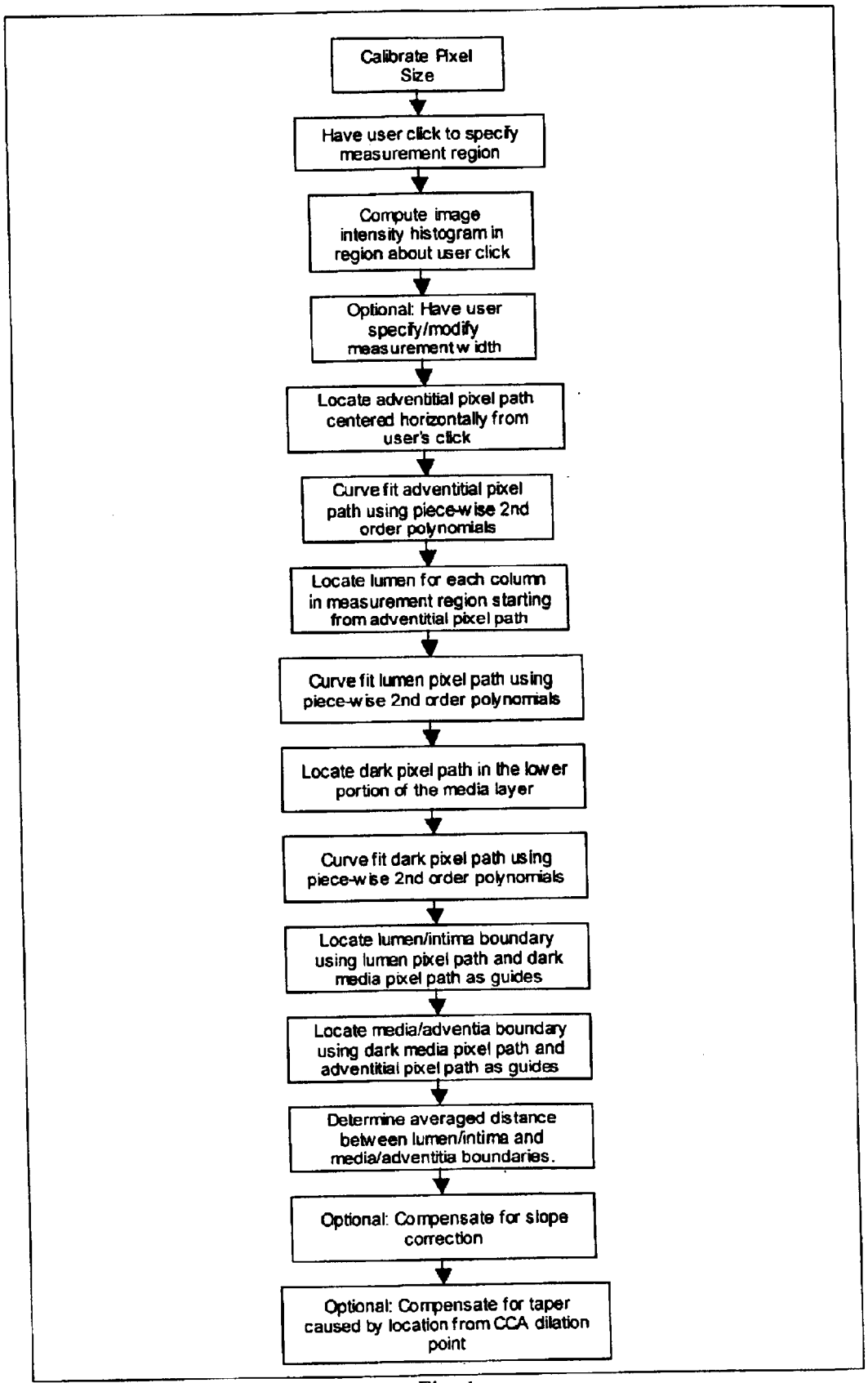
FIG. 1 is flow chart describing an algorithm for measuring an IMT in accordance with the present invention.

FIG. 1 is a flow chart describing an algorithm for measuring IMT via the analysis of digital blood vessel image data generated by an ultrasound generating device scanning the blood vessel with ultrasound. After this image is inputted digitally into a computer, the preferred method is as follows:

1. Calibrating the pixel size.
2. Specifying the measurement region on the computer image.
3. Computing the image intensity histogram in this measurement region.
4. Specifying or modifying the measurement width.
5. Computer locating the adventitial pixel path centered horizontally from measurement region.
6. Curve fitting the adventitial pixel path using piece-wise second order polynomials.
7. Locating and listing the lumen for each column in the measurement region starting from the adventitial pixel path. This is the process for finding the lumen pixel path.
8. Curve fitting the lumen pixel path using piece-wise second order polynomials
9. Locating the dark pixel path in the lower portion of the media layer.
10. Curve fitting the dark pixel path using piece-wise second order polynomials.
11. Locating the lumen/intima boundary via the lumen pixel path and dark pixel path.
12. Locating the media/adventitia boundary via the dark media pixel path and adventitial pixel path.
13. Computer calculating the averaged distance between lumen/intima and media/adventitia boundaries.
14. Optionally compensating for the slope correction.
15. Optionally compensating for taper caused by location from CCA dilation point.

The method thus employs an ultrasound machine for capturing digital images of blood vessels, typically the carotid artery. These digital images of longitudinal views of blood vessels contains dark and light regions in the image, which represent differing densities of tissue. The brightest portion of the ultrasound image corresponds to the densest part of the tissue that is being measured. When capturing a digital image of a blood vessel using ultrasound technology, the brightest portion of the images typically corresponds to the walls of the blood vessel itself, which have three different regions. The portion of the wall of the artery that is adjacent to the blood flow is the intima. The next layer after the intima is the media. Finally, after the media is the adventitia. When viewing an ultrasound image of a blood vessel, the adventitia typically shows up as the brightest portion of the image. Usually the far wall of the blood vessel (the wall furthest from the skin) is the clearest, and hence is typically where the measuring of the IMT is accomplished with the most accurate results. Near wall measurements can also be taken but the clarity, according to physical ultrasound transmission principles, of these images tends to be less distinct than the corresponding far wall site. The small reduction in image clarity is however insufficient to outweigh the benefit of not missing potentially huge differences in IMT due to eccentric layering patterns of atherosclerosis.

Figure 2:
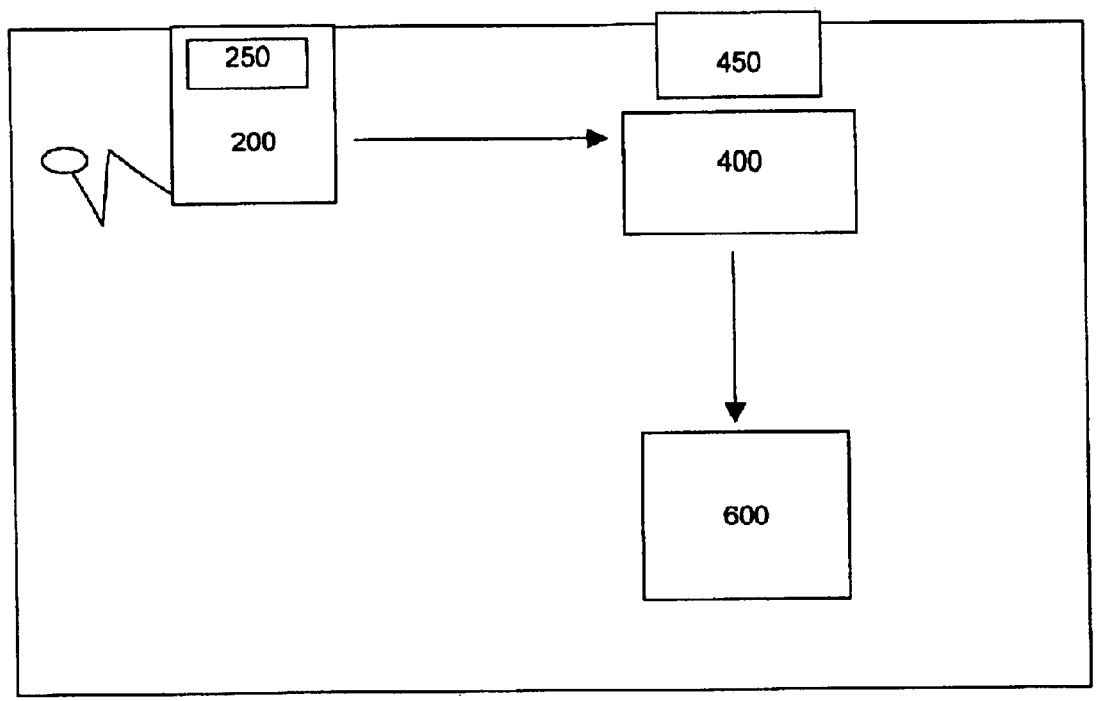
FIG. 2 is a schematic of a preferred embodiment of the apparatus.

FIG. 2 is a schematic of a preferred embodiment of the apparatus. It contains the following components:

- 100—Ultrasound probe
- 200—Ultrasound device that is capable of exporting digitized images of a blood vessel.
- 250—Ultrasound graphical display
- 300—Communication mechanism capable of transferring digital image from ultrasound device to computer's internal hard drive or system RAM. This could be a serial cable, USB cable, hard drive, floppy drive, compact flash media, wireless network, 802.11 network, blue tooth wireless network, etc.
- 400—Computer containing the software application that takes the digitized ultrasound images as input and generates IMT values as well as other useful information as output. This information can be stored on the internal hard drive of the computer. This information could also be displayed on the screen (450) or sent to the printer (600) over the computer/printer communication mechanism (500).
- 450—Computer screen capable of displaying the software application's critical user interface information including methods for allowing operator to control software, methods for allowing the operator to see the results of measuring the IMT and methods for sending the generated information to local or remote destinations (hard drive, printer, etc.).
- 500—Communication mechanism capable of transferring information from the computer to the printer for the purposes of printing reports about the IMT measurement(s) and/or printing useful information about configuration of the software application as well as printing useful information about patient statistics, trends, and other generated data.
- 600—Printing device capable of creating a printed hardcopy output of a IMT report or other printed media.

A preferred embodiment of the apparatus might consist of some or all of the following specific components:

- 100: L-38/10-5: 38 mm broadband linear array ultrasound transducer to be used with a SonoSite 180PLUS ultrasound device.
- 200/250: A SonoSite 180PLUS digital hand-carried ultrasound device.
- 300: USB cable combined with SiteLink Image Manager software installed on computer (400).
- 400/450: Hewlett-Packard laptop computer with 256M RAM, 30 GB hard drive, 14 inch color LCD screen, integrated pointing device
- 500: IEEE 1284 parallel cable (standard parallel printer cable)
- 600: Hewlett-Packard Color LaserJet 4600 color laser printer The device employs in addition, means for transferring image data from ultrasound machine to computer. The computer employs running software application that contains a sophisticated algorithmic based measurement apparatus to measure the intima-media thickness (IMT) of a blood vessel wall using the digital images originating from ultrasound machine. After the analysis is completed, the computer generates a report via an output device to provide a patient with a report stratifying the patient's general atherosclerotic burden and comparing the patient's IMT value with the general population. This report is then added to a computer database to allow the supplementation to the general population data pool as well as to allow patient follow up on how his/her IMT varies over time.

Although this specification has referred to the illustrated embodiments, it is not intended to restrict the scope of the appended claims. The claims themselves recite those features deemed essential to the invention.

We claim:

1. A method for determining the intima-media thickness of the near and/or far wall of a blood vessel comprising:
   a. capturing pixel images from an ultrasound machine's scan of a desired segment of blood vessels and inputting said blood vessel pixel images into a computer,
   b. inputting an analyzer program into the computer which determines the calibrated pixel size of the ultrasound image using at least one of the following mechanisms:
      i. operator specifies two points on the ultrasound image and also specifies the distance between the two specified points, after which the analyzer program computes the calibrated pixel size and assumes this size for both vertical and horizontal dimensions,
      ii. operator specifies two horizontal points as well as the distance between these two horizontal points and also specifies two vertical points and the distance between these two vertical points, after which the analyzer program computes the horizontal calibrated pixel size and the vertical calibrated pixel size,
      iii. the analyzer program recognizes known landmarks and characteristics on the ultrasound image and determines the image from a known ultrasound device with a known zoom/scale factor, and a known distance between found landmarks, to determine how many pixels are between a set of vertical and/or horizontal landmarks without operator intervention,
   c. activating the analyzer program to computer locate via pixel image intensities the lumen/intima and media/adventitia boundaries of a blood vessel's near and/or far wall using at least one of the following operator inputs:
      i. operator specifies a single pixel image position as the analyzer program's horizontal center, left, or right position in the measurement region,
      ii. operator specifies a left, right, and/or overall width constraint
      iii. operator specifies an outer constraint distance, boundary line, multi-segment boundary line, boundary spline curve or polynomial boundary curve to constrain the media/adventitia pixel path to within this boundaries distance from the center of the blood vessel,
      iv. operator specifies an inner constraint distance, boundary line, multi-segment boundary line, boundary spline curve or polynomial boundary curve to constrain the media/adventitia pixel path to no closer than this boundaries distance to the center of the blood vessel,
      v. operator specifies an inner constraint distance, boundary line, multi-segment boundary line, boundary spline curve or polynomial boundary curve to constrain the lumen/intima pixel path to no closer than this boundaries distance to the center of the blood vessel, vi. operator specifies an outer constraint distance, boundary line, multi-segment boundary line, boundary spline curve or polynomial boundary curve to constrain the lumen/intima pixel path to within this boundaries distance from the center of the blood vessel, vii. operator specifies a smoothness factor to determine how jaggy the lumen/intima and/or the media/adventitia pixel paths can be, and d. computer calculating the averaged distance between lumen/intima and media/adventitia boundaries.

2. A method for determining the intima-media thickness of the near and/or far wall of a blood vessel according to claim 1, wherein the analyzer program optionally computes an image intensity histogram covering the entire measurement region which is then used to determine the dynamic range of pixel intensities for the purposes of determining typical lumen pixel value and typical adventitial pixel value for reference points to be used when finding lumen pixel path and adventitial pixel path.

3. A method for determining the intima-media thickness of the near and/or far wall of a blood vessel according to claim 1, wherein the computer program analyzer uses slope correction to compensate for images of blood vessels that are sloping.

4. A method for determining the intima-media thickness of the near and/or far wall of a blood vessel according to claim 1, wherein the computer program analyzer compensates for tapering of the diameter of the vessel as a function of distance from a point of bifurcation splitting from a single vessel into two vessels.

5. A method for determining the intima-media thickness of the near and/or far wall of a blood vessel according to claim 1, including computer generating a report via an output device stratifying the patient's general atherosclerotic burden and/or comparing the patient's IMT value with the general population.

6. A method for determining the intima-media thickness of the near and/or far wall of a blood vessel according to claim 1, including inputting into the computer a database of the intima-media thickness, and possibly the presence of plaque combined with patient information consisting of some or all, but not limited to, age, gender, typical cardiovascular risk factors, and wherein the computer program includes calculations to allow the supplementation and/or augmentation into a general population data pool as well as to allow patient follow up on how a patient's IMT varies over time.

7. A method for determining the intima-media thickness of the near and/or far wall of a blood vessel according to claims 1, including employing any or all of the following to address operator dependent factors that reduce accuracy:

a. minimizing gain between the extremes of high and low of the ultrasound instrument TGC and overall power gain settings, b. compensating for IMT as a function of distance from dilation using the CCA dilation landmark position to the measured IMT segment to account for typical variations in IMT thickness as a function of distance from the dilation point, c. compensating for the probe angle positions in relation to the neck surface during image acquisition because of the anatomically eccentric variation in IMT thickening, d. factoring for the head position during image acquisition, e. ensuring inclusion of near wall measurements for true atherosclerotic burden stratification, f. factoring for ECG synchrony, which varies within each cardiac cycle, and g. compensating for the cross-sectioning of the maximal CCA diameter, when measuring the IMT from an image captured from a cross section view of the vessel that does not include the maximal diameter of the vessel.

8. A method for determining the intima-media thickness of the near and/or far wall of a blood vessel according to claim 1, including manually assisting the automated algorithm in varying steps for images with poor contrast or signal-to-noise ratio where the automated values are obviously in error, by the operator manually assisting in any or all of the following:

a) locating the adventitia, b) locating the lumen, c) determining the curvature/slope of the intima/media layer, d) constraining the search region for the lumen/intima boundary, e) constraining the search region for the media/adventitia boundary, f) increasing, decreasing or laterally moving the region of measurement to find a less noisy region of the intima/media layer, and g) strengthening the aggressiveness (more boldness) with which the various "horizontal" pathways parallel to vessel wall can continue through even lower contrast regions.

9. A method for determining the intima-media thickness of the near and/or far wall of a blood vessel according to claim 1, including computing the intensity histogram in the region of the measured IMT and using this information as a confidence indicator to the operator as to how good the automated algorithm is performing, and if the confidence is too low, the operator manually assists in the IMT measurement or ignores this particular image altogether.

10. A method for determining the intima-media thickness of the near and/or far wall of a blood vessel according to claim 9, wherein the mechanisms that use histogram information as a confidence indicator could include one or more of the following:

a) displaying the histogram to the operator for comparison with a good quality or poor quality histogram, b) generating a numerical correlation between the computed histogram and a known good quality shaped histogram for ultrasound images that the automated measurement system is known to perform well against and displaying the degree to which this computed histogram correlates using one or more of the following display mechanisms:

i. a color coded indicator that varies in colors from a low confidence color like red, to a high confidence color like green, ii. a numerical display of confidence as a percentage, where a low percentage would indicate a poor confidence and a high percentage would indicate a high confidence, and iii. status indicator in the form of a "meter display" that displays the confidence on a range from poor to excellent; and c) Overlaying the computed histogram on top of known baseline good histograms and/or poor histograms to visually correlate how close the computed histogram matches baseline histograms.

11. An apparatus for determining the intima-media thickness of the near and/or far wall of a blood vessel comprising:
   a. means for capturing pixel images from an ultrasound machine's scan of a desired segment of blood vessels and inputting said blood vessel pixel images into
   b. a standalone or embedded computer,
   c. an analyzer program inputted into the standalone or embedded computer which determines the calibrated pixel size of the ultrasound image using at least one of the following mechanisms:
      i. operator specifies two points on the ultrasound image and also specifies the distance between the two specified points, after which the analyzer program computes the calibrated pixel size and assumes this size for both vertical and horizontal dimensions,
      ii. operator specifies two horizontal points as well as the distance between these two horizontal points and also specifies two vertical points and the distance between these two vertical points, after which the analyzer program computes the horizontal calibrated pixel size and the vertical calibrated pixel size,
      iii. the analyzer program recognizes known landmarks and characteristics on the ultrasound image and determines the image is from a known ultrasound device and is also at a known zoom/scale factor and can therefore determine how many pixels are between a set of vertical and/or horizontal landmarks and, since it knows from which ultrasound device the image originated, it knows the distance between the found landmarks, and can therefore computer the calibrated pixel size without operator intervention since it has determined the number of pixels and knows the distance across those pixels,
whereby the analyzer program causes the computer to locate via pixel image intensities the lumen/intima and media/adventitia boundaries of a blood vessel's near and/or far wall using at least one of the following operator inputs:
      i. operator specifies a single pixel image position as the analyzer program's horizontal center, left, or right position in the measurement region,
      ii. operator specifies a left, right, and/or overall width constraint
      iii. operator specifies an outer constraint distance, boundary line, multi-segment boundary line, boundary spline curve or polynomial boundary curve to constrain the media/adventitia pixel path to within this boundaries distance from the center of the blood vessel,
      iv. operator specifies an inner constraint distance, boundary line, multi-segment boundary line, boundary spline curve or polynomial boundary curve to constrain the media/adventitia pixel path to no closer than this boundaries distance to the center of the blood vessel,
      v. operator specifies an inner constraint distance, boundary line, multi-segment boundary line, boundary spline curve or polynomial boundary curve to constrain the lumen/intima pixel path to no closer than this boundaries distance to the center of the blood vessel,
      vi. operator specifies an outer constraint distance, boundary line, multi-segment boundary line, boundary spline curve or polynomial boundary curve to constrain the lumen/intima pixel path to within this boundaries distance from the center of the blood vessel,
      vii. operator specifies a smoothness factor to determine how jaggy the lumen/intima and/or the media/adventitia pixel paths can be,
and calculates the averaged distance between lumen/intima and media/adventitia boundaries.

12. An apparatus for determining the intima-media thickness of the near and/or far wall of a blood vessel according to claim 11, wherein the computer program uses slope correction to compensate for images of blood vessels that are sloping.

13. An apparatus for determining the intima-media thickness of the near and/or far wall of a blood vessel according to claim 11, wherein the computer program compensates for tapering of the diameter of the vessel as a function of distance from a point of bifurcation (splitting from a single vessel into two vessels).

14. An apparatus for determining the intima-media thickness of the near and/or far wall of a blood vessel according to claim 11, including computer generating means to generate a report via an output device stratifying the patient's general atherosclerotic burden and/or comparing the patient's IMT value with the general population.

15. An apparatus for determining the intima-media thickness of the near and/or far wall of a blood vessel according to claim 11, including a computer database wherein the intima-media thickness, and possibly the presence of plaque combined with patient information consisting of some or all, but not limited to, age, gender, typical cardiovascular risk factors is added to allow the supplementation and/or augmentation to the general population data pool as well as to allow patient follow up on how his/her IMT varies over time.

16. An apparatus that determines the intima-media thickness of the near and/or far wall of a blood vessel according to claim 11, wherein the computer program optionally allows manually assisting the automated algorithm in varying steps for images with poor contrast or signal-to-noise ratio where the automated values are obviously in error, by the operator manually assisting in any or all of the following:
   a) locating the adventitia,
   c) locating the lumen,
   c) determining the curvature/slope of the intima/media layer,
   d) constraining the search region for the lumen/intima boundary,
   e) constraining the search region for the media/adventitia boundary,
   f) increasing, decreasing or laterally moving the region of measurement to find a less noisy region of the intima/media layer, and
   g) strengthening the aggressiveness (more boldness) with which the various "horizontal" pathways parallel to vessel wall can continue through even lower contrast regions.

17. An apparatus that determines the intima-media thickness of the near and/or far wall of a blood vessel according to claim 11, wherein the computer program computes the intensity histogram in the region of the measured IMT and uses this information as a confidence indicator to the operator as to how good the automated algorithm is performing, and if the confidence is too low, the operator manually assists in the IMT measurement or ignores this particular image altogether.

18. An apparatus that determines the intima-media thickness of the near and/or far wall of a blood vessel according to claim 17, including program mechanisms that use histogram information as a confidence indicator like one or more of the following:
  a) displaying the histogram to the operator for comparison with a good quality or poor quality histogram,
  b) generating a numerical correlation between the computed histogram and a known good quality shaped histogram for ultrasound images that the automated measurement system is known to perform well against and displaying the degree to which this computed histogram correlates using one or more of the following display mechanisms:
    i. a color coded indicator that varies in colors from a low confidence color like red, to a high confidence color like green,
    ii. a numerical display of confidence as a percentage, where a low percentage would indicate a poor confidence and a high percentage would indicate a high confidence, and
    iii. status indicator in the form of a "meter display" that displays the confidence on a range from poor to excellent; and
  c) overlaying the computed histogram on top of known baseline good histograms and/or poor histograms to visually correlate how close the computed histogram matches baseline histograms.

19. An apparatus for determining the intima-media thickness of the near and/or far wall of a blood vessel according to claim 11, including a conventional global communication network to transmit off-site measurements to a remote location for digital analysis via a modem, network card, blue tooth interface or any other interface hook-ups to any known data transmission networks such as terrestrial and wireless phone networks, optical data transmission networks, local area networks (LAN), wide area networks (WAN) and all other known and unknown transmission networks and mediums to access a central computer.

20. A computer program product embedded on a computer-readable medium for determining the intima-media thickness of the near and/or far wall of a blood vessel comprising:
  a. capturing pixel images from an ultrasound machine's scan of a desired segment of blood vessels and inputting said blood vessel pixel images into a standalone or embedded computer,
  b. determining the calibrated pixel size of the ultrasound image using at least one of the following mechanisms:
    i. operator specifies two points on the ultrasound image and also specifies the distance between the two specified points, after which the analyzer program computes the calibrated pixel size and assumes this size for both vertical and horizontal dimensions,
    ii. operator specifies two horizontal points as well as the distance between these two horizontal points and also specifies two vertical points and the distance between these two vertical points, after which the analyzer program computes the horizontal calibrated pixel size and the vertical calibrated pixel size,
    iii. the analyzer program recognizes known landmarks and characteristics on the ultrasound image and determines the image is from a known ultrasound device and is also at a known zoom/scale factor and can therefore determine how many pixels are between a set of vertical and/or horizontal landmarks and, since it knows from which ultrasound device the image originated, it knows the distance between the found landmarks, and can therefore computer the calibrated pixel size without operator intervention since it has determined the number of pixels and knows the distance across those pixels,
  c. locating via pixel image intensities the lumen/intima and media/adventitia boundaries of a blood vessel's near and/or far wall using one or more of the following operator inputs:
    i. operator specifies a single pixel image position as the analyzer program's horizontal center, left, or right position in the measurement region,
    ii. operator specifies a left, right, and/or overall width constraint
    iii. operator specifies an outer constraint distance, boundary line, multi-segment boundary line, boundary spline curve or polynomial boundary curve to constrain the media/adventitia pixel path to within this boundaries distance from the center of the blood vessel,
    iv. operator specifies an inner constraint distance, boundary line, multi-segment boundary line, boundary spline curve or polynomial boundary curve to constrain the media/adventitia pixel path to no closer than this boundaries distance to the center of the blood vessel,
    v. operator specifies an inner constraint distance, boundary line, multi-segment boundary line, boundary spline curve or polynomial boundary curve to constrain the lumen/intima pixel path to no closer than this boundaries distance to the center of the blood vessel,
    vi. operator specifies an outer constraint distance, boundary line, multi-segment boundary line, boundary spline curve or polynomial boundary curve to constrain the lumen/intima pixel path to within this boundaries distance from the center of the blood vessel,
    vii. operator specifies a smoothness factor to determine how jaggy the lumen/intima and/or the media/adventitia pixel paths can be,
  d. calculating the averaged distance between lumen/intima and media/adventitia boundaries.

21. A computer program product embedded on a computer-readable medium for determining the intima-media thickness of a blood vessel according to claim 20, wherein the analyzer program sequence optionally computes an image intensity histogram covering the entire measurement region which is then used to determine the dynamic range of pixel intensities for the purposes of determining typical lumen pixel value and typical adventitial pixel value for reference points to be used when finding lumen pixel path and adventitial pixel path.

22. A computer program product embedded on a computer-readable medium for determining the intima-media thickness of a blood vessel according to claim 20, wherein the computer program analyzer sequence uses slope correction to compensate for images of blood vessels that are sloping.

23. A computer program product embedded on a computer-readable medium for determining the intima-media thickness of a blood vessel according to claim 20, wherein the computer program analyzer sequence compensates for tapering of the diameter of the vessel as a function of distance from a point of bifurcation splitting from a single vessel into two vessels.

24. A computer program product embedded on a computer-readable medium for determining the intima-media thickness of a blood vessel according to claim 20, wherein the computer program analyzer sequence generates a report via an output device stratifying the patient's general atherosclerotic burden and/or comparing the patient's IMT value with the general population.

25. A computer program product embedded on a computer-readable medium for determining the intima-media thickness of a blood vessel according to claim 20, wherein the computer program analyzer sequence operates on a database inputted into the computer of the intima-media thickness, and possibly the presence of plaque combined with patient information consisting of some or all, but not limited to, age, gender, typical cardiovascular risk factors, to calculate and allow the supplementation and/or augmentation into a general population data pool as well as to allow patient follow up on how a patient's IMT varies over time.

26. A computer program product embedded on a computer-readable medium for determining the intima-media thickness of a blood vessel according to claim 20, wherein the computer program analyzer sequence allows the employment of any or all of the following to address operator dependent factors that reduce accuracy:
  a. minimizing gain between the extremes of high and low of the ultrasound instrument TGC and overall power gain settings,
  b. compensating for IMT as a function of distance from dilation using the CCA dilation landmark position to the measured IMT segment to account for typical variations in IMT thickness as a function of distance from the dilation point,
  c. compensating for the probe angle positions in relation to the neck surface during image acquisition because of the anatomically eccentric variation in IMT thickening,
  d. factoring for the head position during image acquisition,
  e. ensuring inclusion of near wall measurements for true atherosclerotic burden stratification,
  f. factoring for ECG synchrony, which varies within each cardiac cycle, and
  g. compensating for the cross-sectioning of the maximal CCA diameter, when measuring the IMT from an image captured from a cross section view of the vessel that does not include the maximal diameter of the vessel.

27. A computer program product embedded on a computer-readable medium for determining the intima-media thickness of a blood vessel according to claim 20, wherein the computer program analyzer sequence allows manually assisting the automated algorithm in varying steps for images with poor contrast or signal-to-noise ratio where the automated values are obviously in error, by the operator manually assisting in any or all of the following:
  a) locating the adventitia,
  d) locating the lumen,
  c) determining the curvature/slope of the intima/media layer,
  d) constraining the search region for the lumen/intima boundary,
  e) constraining the search region for the media/adventitia boundary,
  f) increasing, decreasing or laterally moving the region of measurement to find a less noisy region of the intima/media layer, and
  g) strengthening the aggressiveness (more boldness) with which the various "horizontal" pathways parallel to vessel wall can continue through even lower contrast regions.

28. A computer program product embedded on a computer-readable medium for determining the intima-media thickness of a blood vessel according to claim 20, including computing the intensity histogram in the region of the measured IMT and using this information as a confidence indicator to the operator as to how good the automated algorithm is performing, and if the confidence is too low, the operator manually assists in the IMT measurement or ignores this particular image altogether.

29. A computer program product embedded on a computer-readable medium for determining the intima-media thickness of a blood vessel according to claim 20, wherein the mechanisms that use histogram information as a confidence indicator could include one or more of the following:
  a) displaying the histogram to the operator for comparison with a good quality or poor quality histogram,
  b) generating a numerical correlation between the computed histogram and a known good quality shaped histogram for ultrasound images that the automated measurement system is known to perform well against and displaying the degree to which this computed histogram correlates using one or more of the following display mechanisms:
    iv. a color coded indicator that varies in colors from a low confidence color like red, to a high confidence color like green,
    v. a numerical display of confidence as a percentage, where a low percentage would indicate a poor confidence and a high percentage would indicate a high confidence, and
    vi. status indicator in the form of a "meter display" that displays the confidence on a range from poor to excellent; and
  c) Overlaying the computed histogram on top of known baseline good histograms and/or poor histograms to visually correlate how close the computed histogram matches baseline histograms.

* * * * *